United States Patent
Douezan et al.

(10) Patent No.: US 12,102,700 B2
(45) Date of Patent: Oct. 1, 2024

(54) FLUID PHOTOPROTECTIVE COMPOSITION

(71) Applicant: L'OREAL, Paris (FR)

(72) Inventors: Stéphane Douezan, Chevilly Larue (FR); Marina Groc-Bidault, Chevilly Larue (FR)

(73) Assignee: L'OREAL, Paris (FR)

( * ) Notice: Subject to any disclaimer, the term of this patent is extended or adjusted under 35 U.S.C. 154(b) by 757 days.

(21) Appl. No.: 17/286,618

(22) PCT Filed: Dec. 16, 2019

(86) PCT No.: PCT/EP2019/085424
§ 371 (c)(1),
(2) Date: Apr. 19, 2021

(87) PCT Pub. No.: WO2020/127100
PCT Pub. Date: Jun. 25, 2020

(65) Prior Publication Data
US 2021/0361540 A1    Nov. 25, 2021

(30) Foreign Application Priority Data

Dec. 21, 2018  (FR) ..................................... 1873993

(51) Int. Cl.
| | | |
|---|---|---|
| A61K 8/04 | (2006.01) | |
| A61K 8/33 | (2006.01) | |
| A61K 8/35 | (2006.01) | |
| A61K 8/365 | (2006.01) | |
| A61K 8/37 | (2006.01) | |
| A61K 8/40 | (2006.01) | |
| A61K 8/49 | (2006.01) | |
| A61Q 17/04 | (2006.01) | |

(52) U.S. Cl.
CPC ................ *A61K 8/046* (2013.01); *A61K 8/33* (2013.01); *A61K 8/35* (2013.01); *A61K 8/365* (2013.01); *A61K 8/37* (2013.01); *A61K 8/40* (2013.01); *A61K 8/4966* (2013.01); *A61Q 17/04* (2013.01); *A61K 2800/87* (2013.01)

(58) Field of Classification Search
CPC . A61K 8/046; A61K 8/33; A61K 8/35; A61K 8/365; A61K 8/37; A61K 8/40; A61K 8/4966; A61K 2800/87; A61K 8/375; A61Q 17/04
See application file for complete search history.

(56) References Cited

U.S. PATENT DOCUMENTS

2015/0010601 A1 * 1/2015 Roudot .................. A61K 8/375
424/59
2015/0265510 A1    9/2015 Johncock et al.

FOREIGN PATENT DOCUMENTS

| DE | 199 04 329 A1 | 8/2000 |
| FR | 2 903 599 A1 | 1/2008 |
| WO | WO 2015/186078 A1 | 12/2015 |
| WO | WO 2017/218390 A1 | 12/2017 |

OTHER PUBLICATIONS

Anonymous, "Mineral Sun Lotion SPF 30", Database GNPD [Online] MINTEL, Oct. 5, 2018, XP055639900.
Anonymous, "Wet Skin Sun Protector Spray SPF 30", Database GNPD [Online] MINTEL, Nov. 23, 2012, XP055639326.
Anonymous, "Water Resistant Sun Spray SPF 30", Database GNPD [Online] MINTEL, Jul. 23, 2018, XP055639387.
Kawa R. et al., "Das Synergistic-Sun-Systems-Konzept Synergien in Der Formulierungswelt Kosmetischer Sonnenschutzprodukte Nutzen", Parfumerie Und Kosmetik, Huethig, Heidelberg, Parfumeria und Kosmetik, vol. 80, No. 3, pp. 17-23, Jan. 1, 1999, XP001117732.

* cited by examiner

*Primary Examiner* — Robert A Wax
*Assistant Examiner* — Quanglong N Truong
(74) *Attorney, Agent, or Firm* — POLSINELLI PC

(57) ABSTRACT

The present invention relates to a fluid composition intended for the protection of keratin materials against ultraviolet radiation, characterized in that it comprises at least:
(a) a photoprotective system capable of screening out UV radiation,
(b) at least one diester of a $C_2$-$C_8$ carboxylic acid and of a $C_1$-$C_4$ alcohol,
(c) at least one diester of a $C_9$-$C_{14}$ carboxylic acid and of a $C_1$-$C_4$ alcohol,
(d) at least one ($C_4$-$C_{26}$) dialkyl ether.

The present invention relates more particularly to aqueous vaporizable compositions in particular in spray form and also to the pressurization devices containing them.

25 Claims, No Drawings

FLUID PHOTOPROTECTIVE COMPOSITION

CROSS REFERENCE TO RELATED APPLICATIONS

This application is a National Phase filing under 35 U.S.C. § 371 of PCT/EP2019/085424 filed on 16 Dec. 2019; which application in turn claims priority to Application No. 1873993 filed in France on 21 Dec. 2018. The entire contents of each application are hereby incorporated by reference.

The present invention relates to a fluid composition, in particular intended for the protection of keratin materials, such as the skin and/or the hair, against ultraviolet radiation, characterized in that it comprises at least one photoprotective system capable of screening out UV radiation, at least two diesters and at least one dialkyl ether.

The present invention relates more particularly to vaporizable fluid compositions, in particular in the form of sprays, comprising the combination of at least one photoprotective system capable of screening out UV radiation, at least two diesters and at least one dialkyl ether.

It also relates to a device comprising at least (A) one reservoir containing at least one vaporizable fluid aqueous composition as defined above and (B) means for pressurizing said composition, in particular of the non-aerosol pump (atomizer) type, or of the aerosol or aerosol-pump type.

It is known that light radiation with wavelengths of between 280 nm and 400 nm permits tanning of the human epidermis and that light rays with wavelengths between 280 and 320 nm, known as UV-B rays, cause skin burns and erythema which can harm the development of a natural tan; this UV-B radiation should thus be screened out.

It is also known that UV-A rays, with wavelengths between 320 and 400 nm, which cause tanning of the skin, are liable to induce adverse changes therein, in particular in the case of sensitive skin or skin that is continually exposed to solar radiation. UV-A rays cause in particular a loss of elasticity of the skin and the appearance of wrinkles leading to premature aging. They promote triggering of the erythemal reaction or amplify this reaction in certain individuals and may even be the cause of phototoxic or photoallergic reactions. It is therefore desirable also to screen out UV-A radiation.

Many cosmetic compositions intended for the photoprotection (UV-A and/or UV-B) of the skin have been provided to date. Fluid formulations that are easy for the users to apply to the skin are most particularly sought.

These fluid antisun compositions are quite often in the form of an emulsion, of oil-in-water type (i.e. a cosmetically acceptable support constituted of an aqueous dispersing continuous phase and of an oily dispersed discontinuous phase), which contains, in varying concentrations, one or more standard lipophilic and/or hydrophilic organic screening agents capable of selectively absorbing the harmful UV radiation, these screening agents (and the amounts thereof) being selected as a function of the desired sun protection factor, the sun protection factor (SPF) being expressed mathematically as the ratio of the dose of UV radiation required to reach the erythema-forming threshold with the UV-screening agent to the dose of the UV radiation required to reach the erythema-forming threshold without the UV-screening agent.

Thus, there is an increasing need for fluid antisun products with a high protection factor. High protection factors may be achieved by incorporating more screening agents at high concentrations. This is not always possible to do, despite the addition of large amounts of screening agents. Furthermore, such amounts can lead to inconvenience in terms of comfort (tacky, rough effect and/or greasy effect).

When these photoprotective compositions are used, a loss of efficiency linked to the conditions of use and to the change in the characteristics of the deposit of formula on the skin often occurs. For example, the screening efficiency is to a large extent guaranteed by good distribution of the UV-screening agents over the skin. However, during the day, this deposit can become non-uniform due to migration of the UV-screening agents on various areas, thus leaving other areas barely covered by the UV-radiation-screening ingredients.

Furthermore, the migration of the product out of the application area can cause a certain amount of inconvenience and discomfort, in particular in the case of migration into the region of the eyes (stinging and/or ocular veil) or of the lips (bitter sensation). The same is true for hair compositions that must spread correctly and be distributed uniformly along the keratin fibers and not run down the forehead, the nape or the face or into the eyes.

To meet these requirements, use is therefore made of formulations that have been thickened by increasing the viscosity of the compositions through the addition of thickening polymers and/or gelling agents.

However, consumers increasingly appreciate using light cosmetics that are easy to apply. Among these products, fluid compositions are, in general, more appreciated by consumers than thicker emulsions because in particular of their pleasant feel and the ease with which they can be applied.

One of the major drawbacks of these compositions is that is difficult to reconcile both a pleasant feel and very easy application with good efficacy of the final product, in particular while limiting the migration of the product out of the application area. The fluidity of the product promotes its migration and can thus impair its efficacy and its comfort of use. Moreover, antisun products presented in spray form are increasingly desired by consumers, due to their ease of use and their cosmetic pleasantness.

Thus, there is still a need to have fluid antisun compositions which are cosmetically pleasant to use and to apply, while at the same time having good cosmetic performance qualities, good performance qualities in terms of efficacy and wear property, that is to say non-migration of the composition out of the application area. These compositions must also preferably be easily vaporizable (sprayable).

In point of fact, after considerable research carried out in the photoprotection field mentioned above, the applicant has discovered, surprisingly, that the combination of at least one photoprotective system capable of screening out UV radiation, of at least two particular esters and of at least one dialkyl ether makes it possible to obtain a stable fluid composition which has a good SPF, good cosmetic properties, limited migration and also excellent sprayability, without the drawbacks stated above.

For the purposes of the invention, the term "fluid composition" will be understood to mean a composition that is not in solid form and of which the viscosity, measured using a Rheomat 180 viscometer at 25° C. at a rotational speed of 200 rpm after 10 minutes of rotation, is less than 2 Pa·s, preferably less than 1 Pa·s.

This discovery forms the basis of the present invention.

Thus, in accordance with a first subject of the present invention, new fluid compositions are provided, which are intended for the protection of keratin materials, such as the skin and/or the hair, against ultraviolet radiation, characterized in that they comprise at least:

(a) a photoprotective system capable of screening out UV radiation,
(b) at least one diester of a $C_2$-$C_8$ carboxylic acid and of a $C_1$-$C_4$ alcohol,
(c) at least one diester of a $C_9$-$C_{14}$ carboxylic acid and of a $C_1$-$C_4$ alcohol,
(d) at least one ($C_4$-$C_{12}$) dialkyl ether.

According to the invention, the term "photoprotective system capable of screening out UV radiation" is generally intended to denote any compound or any combination of compounds which, via mechanisms that are known per se for the absorption and/or reflection and/or scattering of UV-A and/or UV-B radiation, can prevent, or at least limit, the contact of said radiation with a surface (skin, hair) onto which this or these compounds have been applied. In other words, these compounds may be UV-absorbing photoprotective organic screening agents or UV-scattering and/or UV-reflecting mineral (nano)pigments, and also mixtures thereof.

Another further subject of the present invention lies in the use of at least one mixture of the compounds b), c) and d) in a fluid composition preferably comprising, in a physiologically acceptable aqueous support, at least one photoprotective system capable of screening out UV radiation, with the aim of decreasing the migration of the composition on keratin materials such as the skin and/or the hair.

The invention also relates to the use of at least one mixture of the compounds b), c) and d) in a fluid composition comprising at least one photoprotective system capable of screening out UV radiation, with the aim of improving the cosmetic pleasantness and the comfort of use, and more particularly improving the spreading, improving the ocular comfort and decreasing the effect wherein the composition runs on keratin materials.

Preferably, the composition is an oil-in-water emulsion and comprises a physiologically acceptable, in particular cosmetically acceptable, aqueous support.

The term "organic UV-screening agent" is intended to mean any organic compound capable of screening out UV radiation.

The term "keratin materials" is intended to mean the skin, the lips, the hair, the scalp, the eyelashes, the eyebrows, the nails.

The term "physiologically acceptable medium" is intended to mean a non-toxic medium that may be applied to keratin materials, in particular the skin, the lips, the hair, the eyelashes, the eyebrows, the nails. The composition of the invention can in particular constitute a cosmetic or dermatological composition.

This medium generally has a pleasant color, odor and feel and does not cause any unacceptable discomfort (stinging, tautness or redness) liable to discourage the consumer from using this composition.

In the text hereinbelow, unless otherwise indicated, the limits of a range of values are included in that range, notably in the expressions "between" and "ranging from . . . to . . . ".

Moreover, unless otherwise indicated, the expressions "at least one" and "at least" used in the present description are equivalent to the expressions "one or more" and "greater than or equal to", respectively.

Other characteristics, aspects and advantages of the present invention will emerge on reading the detailed description that follows.

According to the invention, the compounds b), c) and d) are liquid and are volatile or nonvolatile, preferably nonvolatile.

Diester b)

According to a particular embodiment of the invention, the diester(s) of a $C_2$-$C_8$ carboxylic acid and of a $C_1$-$C_4$ alcohol b) are chosen from esters of dicarboxylic acids comprising from 2 to 8 carbon atoms, preferably from 4 to 6 atoms, such as for example adipic acid.

According to one preferred embodiment, the diester(s) of a $C_2$-$C_8$ carboxylic acid and of a $C_1$-$C_4$ alcohol b) are chosen from the compounds of formula (I):

R1—O—CO—X—CO—O—R2     (I)

wherein:
R1 and R2, which may be identical or different, are chosen from $C_1$-$C_4$ linear alkyls, $C_3$-$C_4$ branched alkyls and mixtures thereof
X is a $C_2$-$C_6$, preferably $C_2$-$C_4$, linear or branched, preferably linear, hydrocarbon-based divalent radical.
More particularly, R1 and R2 are $C_3$-$C_4$ branched alkyls and preferably isopropyl.

According to the invention, the preferred compound b) is diisopropyl adipate.

Diester c)

According to one particular embodiment of the invention, the diester(s) of a $C_9$-$C_{14}$ carboxylic acid and of a $C_1$-$C_4$ alcohol c) are chosen from esters of dicarboxylic acids comprising from 9 to 14 carbon atoms, preferably from 9 to 12 carbon atoms, such as for example sebacic acid.

According to one preferred embodiment, the diester(s) of a $C_9$-$C_{14}$ carboxylic acid and of a $C_1$-$C_4$ alcohol c) are chosen from the compounds of formula (II):

R1—O—CO—X—CO—O—R2     (II)

wherein:
R1 and R2, which may be identical or different, are chosen from $C_1$-$C_4$ linear alkyls, $C_3$-$C_4$ branched alkyls and mixtures thereof
X is a $C_7$-$C_{12}$, preferably $C_7$-$C_{10}$, linear or branched, preferably linear, hydrocarbon-based divalent radical.
More particularly, R1 and R2 are $C_3$-$C_4$ branched alkyls and preferably isopropyl.

According to the invention, the preferred compound c) is diisopropyl sebacate.

Diether d)

The diether d) is preferably of formula (III),

R5—O—R6     (III)

wherein R5 et R6, which may be identical or different, denote a $C_6$-$C_{25}$, linear or branched alkyl or alkenyl radical.

Preferably, the ether of formula (II) is chosen from the compounds for which the radicals R5 and R6, which may be identical or different, denote a $C_6$-$C_{12}$, linear or branched alkyl or alkenyl radical.

More particularly, according to the present invention, the radicals R5 and R6 are identical.

According to one particular embodiment of the invention, the preferred dialkyl ether is chosen from di-n-hexyl ether, di-n-heptyl ether, di-n-octyl ether, di-n-nonyl ether, di-n-decyl ether, a di-isodecyl ether, a di-n-dodecyl ether, a di-n-eteradecyl ether, a di-n-hexadecyl ether, a di-n-octadecyl ether or a mixture thereof.

R5 and R6 preferentially denote a C radical. These compounds may be prepared according to the process described in patent application DE 41 27 230.

Preferably, the ether d) of formula (III) is the di-n-octyl ether (INCI name: dicaprylyl ether). Such a product is commercially available, for example under the name Cetiol OE from the company BASF, or Rofetan OE from the company Ecogreen Oleochemicals.

The compound b) in accordance with the invention is present in the composition preferably in an amount from 0.1% to 10% by weight and even more preferentially from 0.5% to 8% and even more particularly from 1% to 5% relative to the total weight of the composition.

The compound c) in accordance with the invention is present in the composition preferably in an amount from 0.1% to 10% by weight and even more preferentially from 0.5% to 8% and even more particularly from 1% to 5% relative to the total weight of the composition.

The compound d) in accordance with the invention is present in the composition preferably in an amount from 0.1% to 10% by weight and even more preferentially from 0.5% to 8% and even more particularly from 1% to 5% relative to the total weight of the composition.

Photoprotective System:

According to the invention, the photoprotective system may be formed from one or more hydrophilic, lipophilic or insoluble organic screening agents and/or one or more mineral (nano)pigments. It will preferentially be constituted of at least one hydrophilic, lipophilic or insoluble organic UV-screening agent.

The hydrophilic, lipophilic or insoluble organic UV-screening agents are chosen especially from anthranilates; dibenzoylmethane derivatives; cinnamic derivatives; salicylic derivatives; camphor derivatives; benzophenone derivatives; β,β-diphenylacrylate derivatives; triazine derivatives; benzotriazole derivatives; benzalmalonate derivatives, especially those cited in patent U.S. Pat. No. 5,624,663; benzimidazole derivatives; imidazolines; bis-benzazolyl derivatives as described in patents EP 669 323 and U.S. Pat. No. 2,463,264; p-aminobenzoic acid (PABA) derivatives; methylenebis(hydroxyphenylbenzotriazole) derivatives as described in patent applications U.S. Pat. Nos. 5,237,071, 5,166,355, GB 2 303 549, DE 197 26 184 and EP 893 119; benzoxazole derivatives as described in patent applications EP 0 832 642, EP 1 027 883, EP 1 300 137 and DE 101 62 844; screening polymers and screening silicones such as those described especially in patent application WO 93/04665; α-alkylstyrene-based dimers, such as those described in patent application DE 198 55 649; 4,4-diarylbutadienes such as those described in patent applications EP 0 967 200, DE 197 46 654, DE 197 55 649, EP-A-1 008 586, EP 1 133 980 and EP 133 981, and mixtures thereof.

The compositions according to the invention may also contain one or more UV-screening agents chosen from hydrophilic, lipophilic or insoluble organic UV-screening agents and/or one or more mineral pigments. It will preferentially be constituted of at least one hydrophilic, lipophilic or insoluble organic UV-screening agent.

The term "hydrophilic UV-screening agent" is intended to mean any cosmetic or dermatological organic or inorganic compound for screening out UV radiation, which can be fully dissolved in molecular form in a liquid aqueous phase or else which can be dissolved in colloidal form (for example in micellar form) in a liquid aqueous phase.

The term "lipophilic screening agent" is intended to mean any cosmetic or dermatological organic or inorganic compound for screening out UV radiation, which can be fully dissolved in molecular form in a liquid fatty phase or which can be dissolved in colloidal form (for example in micellar form) in a liquid fatty phase.

The term "insoluble UV-screening agent" is intended to mean any cosmetic or dermatological organic or inorganic compound for screening out UV radiation which has a solubility in water of less than 0.5% by weight and a solubility of less than 0.5% by weight in the majority of organic solvents such as liquid paraffin, fatty alcohol benzoates and fatty acid triglycerides, for example Miglyol 812® sold by the company Dynamit Nobel. This solubility, determined at 70° C., is defined as the amount of product in solution in the solvent at equilibrium with an excess of solid in suspension after returning to ambient temperature. It may be readily evaluated in the laboratory.

The additional organic UV-screening agents are chosen in particular from cinnamic compounds; anthranilate compounds; salicylic compounds; dibenzoylmethane compounds; benzylidenecamphor compounds; benzophenone compounds; β,β-diphenylacrylate compounds; triazine compounds; benzotriazole compounds; benzalmalonate compounds, in particular those cited in patent U.S. Pat. No. 5,624,663; benzimidazole derivatives; imidazoline compounds; bis-benzazolyl compounds, as described in patents EP 669 323 and U.S. Pat. No. 2,463,264; p-aminobenzoic (PABA) compounds; methylenebis(hydroxyphenylbenzotriazole) compounds, as described in patent applications U.S. Pat. Nos. 5,237,071, 5,166,355, GB 2 303 549, DE 197 26 184 and EP 893 119; benzoxazole compounds, as described in patent applications EP 0 832 642, EP 1 027 883, EP 1 300 137 and DE 101 62 844; screening polymers and screening silicones, such as those described in particular in patent application WO 93/04665; α-alkylstyrene-based dimers, such as those described in patent application DE 198 55 649; 4,4-diarylbutadiene compounds, as described in patent applications EP 0 967 200, DE 197 46 654, DE 197 55 649, EP-A-1 008 586, EP 1 133 980 and EP 133 981, and mixtures thereof.

As examples of organic photoprotective agents, mention may be made of those denoted hereinbelow under their INCI name:

Cinnamic Compounds:
  Ethylhexyl methoxycinnamate sold in particular under the trade name Parsol MCX®
  by DSM Nutritional Products,
  Isopropyl methoxycinnamate,
  Isoamyl p-methoxycinnamate, sold under the trade name Neo Heliopan E 1000® by
  Symrise,
  DEA methoxycinnamate,
  Diisopropyl methylcinnamate,
  Glyceryl Ethylhexanoate Dimethoxycinnamate.

Dibenzoylmethane Compounds:
  Butylmethoxydibenzoylmethane, sold in particular under the trade name Parsol 1789® by DSM Nutritional Products,
  Isopropyldibenzoylmethane.

Para-Aminobenzoic Compounds:
  PABA,
  Ethyl PABA,
  Ethyl dihydroxypropyl PABA,
  Ethylhexyl dimethyl PABA, sold in particular under the name Escalol 507® by ISP,
  Glyceryl PABA,
  PEG-25 PABA, sold under the name Uvinul P 25® by BASF.

Salicylic Compounds:
  Homosalate, sold under the name Eusolex HMS® by Rona/EM Industries, Ethylhexyl salicylate, sold under the name Neo Heliopan OS® by Symrise, Dipropylene glycol salicylate, sold under the name Dipsal® by Scher, TEA salicylate, sold under the name Neo Heliopan TS® by Symrise.

β,β-Diphenyl Acrylate Compounds:
  Octocrylene, sold in particular under the trade name Uvinul N 539® by BASF, Etocrylene, sold in particular under the trade name Uvinul N 35® by BASF.
Benzophenone Compounds:
  Benzophenone-1, sold under the trade name Uvinul 400® by BASF,
  Benzophenone-2, sold under the trade name Uvinul D 50® by BASF,
  Benzophenone-3 or Oxybenzone, sold under the trade name Uvinul M 40® by BASF,
  Benzophenone-4, sold under the trade name Uvinul MS 40® by BASF,
  Benzophenone-5,
  Benzophenone-6, sold under the trade name Helisorb 11® by Norquay,
  Benzophenone-8, sold under the trade name Spectra-Sorb UV-24® by American Cyanamid,
  Benzophenone-9, sold under the trade name Uvinul DS 49® by BASF,
  Benzophenone-12,
  n-Hexyl 2-(4-diethylamino-2-hydroxybenzoyl)benzoate, sold under the trade name Uvinul A Plus® or, as a mixture with octyl methoxycinnamate, under the trade name Uvinul A Plus B® by the company BASF,
  1,1'-(1,4-Piperazinediyl)bis[1-[2-[4-(diethylamino)-2-hydroxybenzoyl]phenyl]methanone] (CAS 919803-06-8), as described in patent application WO 2007/071 584; this compound advantageously being used in micronized form (mean size of 0.02 to 2 μm), which may be obtained, for example, according to the micronization process described in patent applications GB-A-2 303 549 and EP-A-893 119, and in particular in the form of an aqueous dispersion.
Benzylidenecamphor Compounds:
  3-Benzylidenecamphor, manufactured under the name Mexoryl SD® by Chimex, 4-Methylbenzylidenecamphor, sold under the name Eusolex 6300® by Merck,
  Benzylidenecamphorsulfonic acid, manufactured under the name Mexoryl SL® by Chimex,
  Camphor benzalkonium methosulfate, manufactured under the name Mexoryl SO® by Chimex,
  Terephthalylidenedicamphorsulfonic acid, manufactured under the name Mexoryl SX® by Chimex,
  Polyacrylamidomethylbenzylidenecamphor, manufactured under the name Mexoryl SW® by Chimex.
Phenylbenzimidazole Compounds:
  Phenylbenzimidazolesulfonic acid, sold in particular under the trade name Eusolex 232® by Merck.
Bis-Benzoxazolyl Compounds
  Disodium phenyl dibenzimidazole tetrasulfonate sold under the trade name Neo Heliopan AP® by Haarmann and Reimer.
Phenylbenzotriazole Compounds:
  Drometrizole trisiloxane, sold under the name Silatrizole® by Rhodia Chimie.
Methylenebis(Hydroxyphenylbenzotriazole) Compounds:
  Methylenebis(benzotriazolyl)tetramethylbutylphenol, in particular in solid form, such as the product sold under the trade name Mixxim BB/100® by Fairmount Chemical, or in the form of an aqueous dispersion of micronized particles with an average particle size ranging from 0.01 to 5 μm, more preferentially from 0.01 to 2 μm and more particularly from 0.020 to 2 μm, with at least one alkylpolyglycoside surfactant having the structure $C_nH_{2n+1}O(C_6H_{10}O_5)_xH$, wherein n is an integer from 8 to 16 and x is the mean degree of polymerization of the $(C_6H_{10}O_5)$ unit and ranges from 1.4 to 1.6, as described in patent GB-A-2 303 549, sold in particular under the trade name Tinosorb M® by BASF, or in the form of an aqueous dispersion of micronized particles with an average particle size ranging from 0.02 to 2 μm, more preferentially from 0.01 to 1.5 μm and more particularly from 0.02 to 1 μm, in the presence of at least one polyglyceryl mono($C_8$-$C_{20}$)alkyl ester with a degree of glycerol polymerization of at least 5, such as the aqueous dispersions described in patent application WO 2009/063 392.
Triazine Compounds:
  Bis-ethylhexyloxyphenol methoxyphenyl triazine, sold under the trade name Tinosorb S® by BASF,
  Ethylhexyltriazone sold in particular under the trade name Uvinul T 150® by BASF,
  Diethylhexyl butamido triazone, sold under the trade name Uvasorb HEB® by Sigma 3V,
  2,4,6-tris(dineopentyl 4'-aminobenzalmalonate)-s-triazine,
  2,4,6-tris(diisobutyl 4'-aminobenzalmalonate)-s-triazine,
  2,4-bis(n-butyl 4'-aminobenzoate)-6-(aminopropyltrisiloxane)-s-triazine,
  2,4-bis(dineopentyl 4'-aminobenzalmalonate)-6-(n-butyl 4'-aminobenzoate)-s-triazine,
  symmetrical triazine screening agents substituted with naphthalenyl groups or polyphenyl groups described in patent U.S. Pat. No. 6,225,467, patent application WO 2004/085 412 (see compounds 6 and 9) or the document "Symmetrical Triazine Derivatives", IP.COM IPCOM000031257 Journal, INC West Henrietta, NY, US (20 Sep. 2004), in particular 2,4,6-tris(diphenyl) triazine and 2,4,6-tris(terphenyl)triazine, which is also mentioned in patent applications WO 06/035 000, WO 06/034 982, WO 06/034 991, WO 06/035 007, WO 2006/034 992 and WO 2006/034 985, these compounds advantageously being used in micronized form (mean particle size of 0.02 to 3 μm), which may be obtained, for example, according to the micronization process described in patent applications GB-A-2 303 549 and EP-A-893 119, and in particular in aqueous dispersion form,
  silicone triazines substituted with two aminobenzoate groups, as described in patent EP 0 841 341, in particular 2,4-bis(n-butyl 4'-aminobenzalmalonate)-6-[(3-{1,3,3,3-tetramethyl-1-[(trimethylsilyloxy]disiloxanyl}propyl)amino]-s-triazine.
Anthranilic Compounds:
  Menthyl anthranilate, sold under the trade name Neo Heliopan MA® by Symrise.
Imidazoline Compounds:
  Ethylhexyl dimethoxybenzylidene dioxoimidazoline propionate.
Benzalmalonate Compounds:
  Polyorganosiloxane comprising benzalmalonate functions, such as Polysilicone-15, sold under the trade name Parsol SLX® by Hoffmann-La Roche.
4,4-Diarylbutadiene Compounds:
  1,1-Dicarboxy(2,2'-dimethylpropyl)-4,4-diphenylbutadiene.
Benzoxazole Compounds:
  2,4-Bis[5-1(dimethylpropyl)benzoxazol-2-yl(4-phenyl)imino]-6-(2-ethylhexyl)imino-1,3,5-triazine, sold under the name Uvasorb K2A® by Sigma 3V.

The preferential organic screening agents are chosen from:
- Ethylhexyl methoxycinnamate,
- Ethylhexyl salicylate,
- Homosalate,
- Butyl methoxydibenzoylmethane,
- Octocrylene,
- Phenylbenzimidazolesulfonic acid,
- Benzophenone-3,
- Benzophenone-4,
- Benzophenone-5,
- n-Hexyl 2-(4-diethylamino-2-hydroxybenzoyl)benzoate,
- 4-Methylbenzylidenecamphor,
- Terephthalylidenedicamphorsulfonic acid,
- Disodium phenyldibenzimidazoletetrasulfonate,
- Methylenebis(benzotriazolyl)tetramethylbutylphenol,
- Bis-ethylhexyloxyphenol methoxyphenyl triazine,
- Ethylhexyl triazone,
- Diethylhexyl butamidotriazone,
- 2,4,6-Tris(dineopentyl 4'-aminobenzalmalonate)-s-triazine,
- 2,4,6-Tris(diisobutyl 4'-aminobenzalmalonate)-s-triazine,
- 2,4-Bis(n-butyl 4'-aminobenzoate)-6-(aminopropyltrisiloxane)-s-triazine,
- 2,4-Bis(dineopentyl 4'-aminobenzalmalonate)-6-(n-butyl 4'-aminobenzoate)-s-triazine,
- 2,4-Bis(n-butyl 4'-aminobenzalmalonate)-6-[(3-{1,3,3,3-tetramethyl-1-[(trimethylsilyl)oxy]disiloxanyl}propyl)amino]-s-triazine,
- 2,4,6-Tris(diphenyl)triazine,
- 2,4,6-Tris(terphenyl)triazine,
- Drometrizole trisiloxane,
- Polysilicone-15,
- 1,1-Dicarboxy(2,2'-dimethylpropyl)-4,4-diphenylbutadiene,
- 2,4-bis[5-(1-Dimethylpropyl)benzoxazol-2-yl-(4-phenyl)imino]-6-(2-ethylhexyl)imino-1,3,5-triazine,
- and mixtures thereof.

The particularly preferred organic screening agents are chosen from:
- Ethylhexyl salicylate,
- Homosalate,
- Butyl methoxydibenzoylmethane,
- Octocrylene,
- n-Hexyl 2-(4-diethylamino-2-hydroxybenzoyl)benzoate,
- Terephthalylidenedicamphorsulfonic acid,
- Bis-ethylhexyloxyphenol methoxyphenyl triazine,
- Ethylhexyl triazone,
- Diethylhexyl butamidotriazone,
- 2,4-Bis(n-butyl 4'-aminobenzalmalonate)-6-[(3-{1,3,3,3-tetramethyl-1-[(trimethylsilyl)oxy]disiloxanyl}propyl)amino]-s-triazine,
- Drometrizole trisiloxane,
- and mixtures thereof.

The inorganic UV-screening agents used in accordance with the present invention are metal oxide pigments. More preferentially, the inorganic UV-screening agents of the invention are metal oxide particles with a mean elementary particle size of less than or equal to 0.5 µm, more preferentially between 0.005 and 0.5 µm, even more preferentially between 0.01 and 0.2 µm, better still between 0.01 and 0.1 µm and more particularly between 0.015 and 0.05 µm.

They may be chosen in particular from titanium oxide, zinc oxide, iron oxide, zirconium oxide and cerium oxide, or mixtures thereof.

Such coated or uncoated metal oxide pigments are described in particular in patent application EP-A-0 518 773. Commercial pigments that may be mentioned include the products sold by the companies Sachtleben Pigments, Tayca, Merck and Degussa.

The metal oxide pigments may be coated or uncoated.

The coated pigments are pigments that have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminum salts of fatty acids, metal alkoxides (of titanium or aluminum), polyethylene, silicones, proteins (collagen, elastin), alkanolamines, silicon oxides, metal oxides or sodium hexametaphosphate.

The coated pigments are more particularly titanium oxides that have been coated:
- with silica, such as the product Sunveil® from the company Ikeda,
- with silica and iron oxide, such as the product Sunveil F® from the company Ikeda,
- with silica and alumina, such as the products Microtitanium Dioxide MT 500 SA® and Microtitanium Dioxide MT 100 SA from the company Tayca and Tioveil from the company Tioxide,
- with alumina, such as the products Tipaque TTO-55 (B)® and Tipaque TTO-55 (A)® from the company Ishihara and UVT 14/4 from the company Sachtleben Pigments,
- with alumina and aluminum stearate, such as the products Microtitanium Dioxide MT 100 T®, MT 100 TX®, MT 100 Z® and MT-01® from the company Tayca, the products Solaveil CT-10 W® and Solaveil CT 100® from the company Uniqema and the product Eusolex T-AVO® from the company Merck,
- with silica, alumina and alginic acid, such as the product MT-100 AQ® from the company Tayca,
- with alumina and aluminum laurate, such as the product Microtitanium Dioxide MT 100 S® from the company Tayca,
- with iron oxide and iron stearate, such as the product Microtitanium Dioxide MT 100 F® from the company Tayca,
- with zinc oxide and zinc stearate, such as the product BR 351® from the company Tayca,
- with silica and alumina and treated with a silicone, such as the products Microtitanium Dioxide MT 600 SAS®, Microtitanium Dioxide MT 500 SAS® or Microtitanium Dioxide MT 100 SAS® from the company Tayca,
- with silica, alumina and aluminum stearate and treated with a silicone, such as the product STT-30-DS® from the company Titan Kogyo,
- with silica and treated with a silicone, such as the product UV-Titan X 195® from the company Sachtleben Pigments,
- with alumina and treated with a silicone, such as the products Tipaque TTO-55 (S)® from the company Ishihara or UV Titan M 262® from the company Sachtleben Pigments,
- with triethanolamine, such as the product STT-65-S from the company Titan Kogyo,
- with stearic acid, such as the product Tipaque TTO-55 (C)® from the company Ishihara,
- with sodium hexametaphosphate, such as the product Microtitanium Dioxide MT 150 W® from the company Tayca,
- $TiO_2$ treated with octyltrimethylsilane, sold under the trade name T 805® by the company Degussa Silices, TiO₂ treated with a polydimethylsiloxane, sold under the trade name 70250 Cardre UF TiO2SI3® by the company Cardre, anatase/rutile TiO₂ treated with a polydimethylhydrogenosiloxane, sold under the trade name Microtitanium Dioxide USP Grade Hydrophobic® by the company Color Techniques.

TiO₂ coated with triethylhexanoin, with aluminum stearate and with alumina sold under the trade name Solaveil CT-200-LQ-(WD) by Croda, TiO₂ coated with aluminum stearate, with alumina and with silicone sold under the trade name Solaveil CT-12W-LQ-(WD) by Croda, TiO₂ coated with lauroyl lysine sold by Daito Kasei Kogyo under the name LL 5 Titanium Dioxyde CR 50, TiO₂ coated with C9-15 fluoroalcohol phosphate and with aluminum hydroxide sold by Daito Kasei Kogyo under the name PFX-5 TiO2 CR-50.

Mention may also be made of TiO₂ pigments doped with at least one transition metal such as iron, zinc or manganese and more particularly manganese. Preferably, said doped pigments are in the form of an oily dispersion. The oil present in the oily dispersion is preferably chosen from triglycerides including those of capric/caprylic acids. The oily dispersion of titanium oxide particles may also comprise one or more dispersants, for instance a sorbitan ester, for instance sorbitan isostearate, or a polyoxyalkylenated fatty acid ester of glycerol, for instance TRI-PPG-3 myristyl ether citrate and polyglyceryl-3 polyricinoleate. Preferably, the oily dispersion of titanium oxide particles comprises at least one dispersant chosen from polyoxyalkylenated fatty acid esters of glycerol. Mention may be made more particularly of the oily dispersion of TiO₂ particles doped with manganese in capric/caprylic acid triglyceride in the presence of TRI-PPG-3 myristyl ether citrate and polyglyceryl-3 polyricinoleate and sorbitan isostearate having the INCI name: titanium dioxide (and) TRI-PPG-3 myristyl ether citrate (and) polyglyceryl-3 ricinoleate (and) sorbitan isostearate, for instance the product sold under the trade name Optisol TD50® by the company Croda.

The uncoated titanium oxide pigments are sold, for example, by the company Tayca under the trade names Microtitanium Dioxide MT 500 B or Microtitanium Dioxide MT 600 B®, by the company Degussa under the name P 25, by the company Wacker under the name Transparent titanium oxide PW®, by the company Miyoshi Kasei under the name UFTR®, by the company Tomen under the name ITS® and by the company Tioxide under the name Tioveil AQ.

The uncoated zinc oxide pigments are, for example:
those sold under the name Z-Cote by the company Sunsmart;
those sold under the name Nanox® by the company Elementis;
those sold under the name Nanogard WCD 2025® by the company Nanophase Technologies.

The coated zinc oxide pigments are, for example:
those sold under the name Oxide Zinc CS-5® by the company Toshibi (ZnO coated with polymethylhydrogenosiloxane);
those sold under the name Nanogard Zinc Oxide FN® by the company Nanophase Technologies (as a 40% dispersion in Finsolv TN®, C₁₂-C₁₅ alkyl benzoate);
those sold under the name Daitopersion Zn-30® and Daitopersion Zn-50® by the company Daito (dispersions in cyclopolymethylsiloxane/oxyethylenated polydimethylsiloxane, containing 30% or 50% of zinc oxides coated with silica and polymethylhydrogenosiloxane);
those sold under the name NFD Ultrafine ZnO® by the company Daikin (ZnO coated with perfluoroalkyl phosphate and copolymer based on perfluoroalkylethyl as a dispersion in cyclopentasiloxane);
those sold under the name SPD-Z1® by the company Shin-Etsu (ZnO coated with silicone-grafted acrylic polymer, dispersed in cyclodimethylsiloxane);
those sold under the name Escalol Z100® by the company ISP (alumina-treated ZnO dispersed in the ethylhexyl methoxycinnamate/PVP-hexadecene copolymer/methicone mixture);
those sold under the name Fuji ZnO-SMS-10® by the company Fuji Pigment (ZnO coated with silica and polymethylsilsesquioxane);
those sold under the name Nanox Gel TN® by the company Elementis (ZnO dispersed at a concentration of 55% in C₁₂-C₁₅ alkyl benzoate with hydroxystearic acid polycondensate).

The uncoated cerium oxide pigments may be, for example, those sold under the name Colloidal Cerium Oxide® by the company Rhône-Poulenc.

The uncoated iron oxide pigments are sold, for example, by the company Arnaud under the names Nanogard WCD 2002® (FE 45B®), Nanogard Iron FE 45 BL AQ, Nanogard FE 45R AQ® and Nanogard WCD 2006® (FE 45R®) or by the company Mitsubishi under the name TY-220®.

The coated iron oxide pigments are sold, for example, by the company Arnaud under the names Nanogard WCD 2008 (FE 45B FN)®, Nanogard WCD 2009® (FE 45B 556®), Nanogard FE 45 BL 345® and Nanogard FE 45 BL® or by the company BASF under the name Transparent Iron Oxide®.

Mention may also be made of mixtures of metal oxides, especially of titanium dioxide and of cerium dioxide, including the equal-weight mixture of titanium dioxide and cerium dioxide coated with silica, sold by the company Ikeda under the name Sunveil A®, and also the mixture of titanium dioxide and zinc dioxide coated with alumina, silica and silicone, such as the product M 261® sold by the company Sachtleben Pigments, or coated with alumina, silica and glycerol, such as the product M 211® sold by the company Sachtleben Pigments.

According to the invention, coated or uncoated titanium oxide pigments are particularly preferred.

The photoprotective system according to the invention is preferably present in the compositions according to the invention in a content ranging from 0.1% to 40% by weight and in particular from 5% to 25% by weight relative to the total weight of the composition.

The compositions according to the invention can also comprise agents for the artificial tanning and/or browning of the skin (self-tanning agents) and more particularly dihydroxyacetone (DHA). They are preferably present in amounts ranging from 0.1% to 10% by weight relative to the total weight of the composition.

The aqueous compositions in accordance with the present invention can additionally comprise conventional cosmetic adjuvants chosen in particular from fatty substances, organic solvents, ionic or nonionic and hydrophilic or lipophilic thickeners, softening agents, humectants, opacifiers, stabilizing agents, emollients, silicones, antifoaming agents, fragrances, preservatives, anionic, cationic, nonionic, zwitterionic or amphoteric surfactants, active agents, self-tanning agents, fillers, polymers, propellants, basifying or acidifying agents or any other ingredient commonly used in the cosmetics and/or dermatological field.

Mention may be made, among organic solvents, of lower alcohols and polyols. The latter may be chosen from glycols and glycol ethers, for instance ethylene glycol, propylene glycol, butylene glycol, dipropylene glycol or diethylene glycol.

Hydrophilic thickeners that may be mentioned include carboxyvinyl polymers such as the Carbopol products (carbomers) and the Pemulen products (acrylate/$C_{10}$-$C_{30}$-alkylacrylate copolymer); polyacrylamides, for instance the crosslinked copolymers sold under the names Sepigel 305 (CTFA name: polyacrylamide/$C_{13}$-14 isoparaffin/Laureth 7) or Simulgel 600 (CTFA name: acrylamide/sodium acryloyldimethyltaurate copolymer/isohexadecane/polysorbate 80) by the company SEPPIC; 2-acrylamido-2-methylpropanesulfonic acid polymers and copolymers, optionally crosslinked and/or neutralized, for instance poly(2-acrylamido-2-methylpropanesulfonic acid) sold by the company Hoechst under the trade name Hostacerin AMPS (CTFA name: ammonium polyacryloyldimethyl taurate or Simulgel 800 sold by the company SEPPIC (CTFA name: sodium polyacryolyldimethyltaurate/polysorbate 80/sorbitan oleate); copolymers of 2-acrylamido-2-methylpropanesulfonic acid and of hydroxyethyl acrylate, for instance Simulgel NS and Sepinov EMT 10 sold by the company SEPPIC; cellulose derivatives such as hydroxyethylcellulose; polysaccharides and in particular gums such as xanthan gum; and mixtures thereof.

Lipophilic thickeners that may be mentioned include synthetic polymers such as poly($C_{10}$-$C_{30}$ alkyl acrylates) sold under the name Intelimer IPA 13-1 and Intelimer IPA 13-6 by the company Landec, or modified clays such as hectorite and derivatives thereof, for instance the products sold under the name Bentone.

Needless to say, those skilled in the art will take care to select the abovementioned optional additional compound(s) and/or the amounts thereof so that the advantageous properties intrinsically associated with the compositions in accordance with the invention are not, or not substantially, adversely affected by the envisaged addition(s).

The compositions according to the invention may be prepared according to the techniques that are well known to those skilled in the art. They may in particular be in the form of a simple or complex emulsion (O/W, W/O, O/W/O or W/O/W) such as a cream, a milk or a cream-gel; in the form of an aqueous gel; in the form of a lotion. They may optionally be packaged in aerosol form and may be in the form of a mousse or a spray.

Preferably, the compositions according to the invention are in the form of an oil-in-water or water-in-oil emulsion.

The emulsions generally contain at least one emulsifier chosen from amphoteric, anionic, cationic or nonionic emulsifiers, used alone or as a mixture. The emulsifiers are chosen in an appropriate manner according to the emulsion to be obtained (W/O or O/W emulsion). The emulsions may also contain stabilizers of other types, for instance fillers, or gelling or thickening polymers.

As emulsifying surfactants that may be used for the preparation of the W/O emulsions, examples that may be mentioned include sorbitan, glycerol or sugar alkyl esters or ethers; silicone surfactants, for instance dimethicone copolyols, such as the mixture of cyclomethicone and of dimethicone copolyol, sold under the name DC 5225 C by the company Dow Corning, and alkyldimethicone copolyols such as lauryl methicone copolyol sold under the name Dow Corning 5200 Formulation Aid by the company Dow Corning; cetyl dimethicone copolyol, such as the product sold under the name Abil EM 90R by the company Goldschmidt, and the mixture of cetyl dimethicone copolyol, of polyglyceryl isostearate (4 mol) and of hexyl laurate, sold under the name Abil WE O9 by the company Goldschmidt. One or more coemulsifiers, which may be chosen advantageously from the group comprising polyol alkyl esters, may also be added thereto.

Polyol alkyl esters that may especially be mentioned include polyethylene glycol esters, for instance PEG-30 dipolyhydroxystearate, such as the product sold under the name Arlacel P135 by the company ICI.

Glycerol and/or sorbitan esters that may be mentioned include, for example, polyglyceryl isostearate, such as the product sold under the name Isolan GI 34 by the company Goldschmidt, sorbitan isostearate, such as the product sold under the name Arlacel 987 by the company ICI, sorbitan glyceryl isostearate, such as the product sold under the name Arlacel 986 by the company ICI, and mixtures thereof.

For the O/W emulsions, examples of emulsifiers that may be mentioned include nonionic emulsifiers such as oxyalkylenated (more particularly polyoxyethylenated) esters of fatty acids and of glycerol; oxyalkylenated esters of fatty acids and of sorbitan; oxyalkylenated (oxyethylenated and/or oxypropylenated) esters of fatty acids, such as the PEG-100 stearate/glyceryl stearate mixture sold, for example, by the company ICI under the name Arlacel 165; oxyalkylenated (oxyethylenated and/or oxypropylenated) ethers of fatty alcohols; esters of sugars, such as sucrose stearate; or ethers of fatty alcohol and of sugar, in particular alkyl polyglucosides (APGs), such as decyl glucoside and lauryl glucoside, sold, for example, by the company Henkel under the respective names Plantaren 2000 and Plantaren 1200, cetostearyl glucoside, optionally as a mixture with cetostearyl alcohol, sold, for example, under the name Montanov 68 by the company SEPPIC, under the name Tegocare CG90 by the company Goldschmidt and under the name Emulgade KE3302 by the company Henkel, and also arachidyl glucoside, for example in the form of the mixture of arachidyl alcohol, behenyl alcohol and arachidyl glucoside, sold under the name Montanov 202 by the company SEPPIC. According to one particular embodiment of the invention, the mixture of the alkylpolyglucoside as defined above with the corresponding fatty alcohol may be in the form of a self-emulsifying composition, for example as described in WO-A-92/06778.

The compositions according to the invention find their application in a large number of treatments, in particular cosmetic treatments, for the skin, the lips and the hair, including the scalp, in particular for protecting and/or caring for the skin, the lips and/or the hair, and/or for making up the skin and/or the lips.

Another subject of the present invention is constituted of the use of the compositions according to the invention as defined above for the manufacture of products for the cosmetic treatment of the skin, the lips, the nails, the hair, the eyelashes, the eyebrows and/or the scalp, in particular care products, antisun products and makeup products.

According to one preferred form, the viscosity of the compositions, measured using a Rheomat 180 viscometer at 25° C. at the rotational speed of 200 rpm, after 30 seconds of rotation is less than or equal to 1 Pa·s.

According to one particularly preferred form, the viscosity of the compositions, measured using a Rheomat 180 viscometer at 25° C. at the rotational speed of 200 rpm, after 30 seconds of rotation is less than or equal to 0.5 Pa·s and more particularly from 0.01 to 0.2 Pa·s.

According to one particularly preferred form, the compositions according to the invention are in the form of a vaporizable fluid applied to keratin materials, in particular the skin or the hair in the form of fine particles by means of pressurization devices.

According to the invention, the term "vaporizable composition" is generally intended to denote any composition that is capable of producing fine particles, under pressure in a suitable device.

The present invention also relates to a pressurization device comprising at least (A) one reservoir containing at least one vaporizable fluid composition comprising, in a cosmetically acceptable aqueous support, at least:
- (a) a photoprotective system capable of screening out UV radiation;
- (b) at least one diester of a $C_2$-$C_8$ carboxylic acid and of a $C_1$-$C_4$ alcohol,
- (c) at least one diester of a $C_9$-$C_{14}$ carboxylic acid and of a $C_1$-$C_4$ alcohol,
- (d) at least one ($C_4$-$C_{26}$) dialkyl ether;

as defined above;

and (B) means for pressurizing said composition.

The devices in accordance with the invention are well known to those skilled in the art and comprise non-aerosol pumps or "atomizers", one-compartment or two-compartment aerosol containers comprising a propellant and also aerosol pumps using compressed air as propellant. The latter are described in patents U.S. Pat. Nos. 4,077,441 and 4,850,517 (forming an integral part of the content of the description).

The compositions conditioned as one-compartment aerosols in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

The two-compartment aerosols are equipped with a pocket containing the composition in accordance with the invention. The propellant is located in the can and to the exterior of the pocket. It remains inside the device during use and exerts a pressure on the pocket. This propellant may be a liquefied gas such as the propellants used in one-compartment aerosols, but also a compressed gas such as air or nitrogen.

The concrete but in no way limiting examples illustrating the invention will now be given. The invention will now be described with reference to the examples that follow, which are given as non-limiting illustrations.

In these examples, unless otherwise indicated, the amounts are expressed as weight percentages.

The following antisun formulations were prepared; the amounts are indicated as weight percentages:

EXAMPLES A to E

Vaporizable fluid antisun formulations containing the following ingredients were prepared:

| INCI Name | Phase | A | B | C | D of the invention | E of the invention |
|---|---|---|---|---|---|---|
| AQUA | A1 | 43.73 | 43.73 | 43.73 | 43.73 | 43.73 |
| PROPANEDIOL | A1 | 2.5 | 2.5 | 2.5 | 2.5 | 2.5 |
| GLYCEROL | A1 | 6.0 | 6.0 | 6.0 | 6.0 | 6.0 |
| TRISODIUM ETHYLEDIAMINE DISUCCINATE | A1 | 0.3 | 0.3 | 0.3 | 0.3 | 0.3 |
| ACRYLATES COPOLYMER (AQUA SF1) | A1 | 2.0 | 2.0 | 2.0 | 2.0 | 2.0 |
| TRIETHANOLAMINE | A1 | 0.1 | 0.1 | 0.1 | 0.1 | 0.1 |
| BUTYLMETHOXYDIBENZOYL METHANE | B | 5 | 5 | 5 | 5 | 5 |
| ETHYLHEXYL SALICYLATE | B | 5 | 5 | 5 | 5 | 5 |
| ETHYLHEXYL TRIAZONE | B | 2 | 2 | 2 | 2 | 2 |
| OCTOCRYLENE | B | 2 | 2 | 2 | 2 | 2 |
| HOMOSALATE | B | 10 | 10 | 10 | 10 | 10 |
| DROMETRIZOLE TRISOLOXANE | B | 1.5 | 1.5 | 1.5 | 1.5 | 1.5 |
| BIS-ETHYLHEXYLOXYPHENOL METHOXYOPHENYL TRIAZINE (TINOSORB S from BASF) | B | 4 | 4 | 4 | 4 | 4 |
| C12-22 ALKYL ACRYLATE/HYDROXYETHYLACRYLATE COPOLYMER | B | 2 | 2 | 2 | 2 | 2 |
| DIISOPROPYL ADIPATE | B | | 10 | | 4 | 2 |
| DICAPRYLYL ETHER | B | | | 10 | 3 | 2 |
| DIISOPROPYL SEBACATE | B | 10 | | | 3 | 6 |
| PHENOXYETHANOL | B | 0.5 | 0.5 | 0.5 | 0.5 | 0.5 |
| CAPRYLYL GLYCOL | B | 0.3 | 0.3 | 0.3 | 0.3 | 0.3 |
| CITRIC ACID | C | 0.07 | 0.07 | 0.07 | 0.07 | 0.07 |
| DENATURED ALCOHOL (absolute ethanol) | D | 3 | 3 | 3 | 3 | 3 |

Compositions A to E are prepared according to the following protocol:

Preparation of Phase A1

The starting materials of A1 are weighed out carefully beforehand using a balance (precision=0.01 g), and are heated to a temperature of 65° C. in a tank of a cos 1000 with a jacket.

Preparation of Phase B

Phase B is heated to 80-85° C., cooled to 65° C., and introduced into phase A1 with turbine stirring of Turrax type and scraper blades.

The stirring is maintained for 10 minutes.

The preparation is brought back to ambient temperature with turbine stirring for 10 minutes.

Addition of Phases C, D, E

Phases C and D are successively introduced every 5 minutes into phase (A1+B) with stirring (turbine+scraper blades).

Viscosity

The viscosities of compositions A to E were measured by means of a Rheomat 180 viscometer at 25° C. at the rotational speed of 200 rpm after 10 minutes.

SPF Determination

For each of the compositions A to E, the sun protection factor (SPF) associated therewith was then determined. Said sun protection factor was determined using the in vitro method described by B. L. Diffey et al. in J. Soc. Cosmet. Chem. 40 127-133 (1989); this method consists in determining the monochromatic protection factors over a wavelength range from 290 to 400 nm and in calculating therefrom the sun protection factor according to a given mathematical equation. The measurement was taken with a 1 nm increment on a UV-2000S machine from the company Labsphere, 1.3 mg/cm$^2$ of product being spread on a frosted PMMA plate. The results (mean value corresponding to 5 plates per product, 8 points per plate) are collated in table (I) below:

Protocol for Evaluating Migration

The migration is evaluated in the following way:

10 µl of composition are deposited by means of an Eppendorf micropipette onto a circular surface 25 mm in diameter, on a block of PMMA.

A template is placed below in order to simulate the placement.

Two opposite diameters which make it possible to calculate the surface area of the spreading are accurately measured.

The diameters of the deposit are taken at T0 using a graduated ruler on 2 diagonals.

The initial surface area of the deposit S0 is calculated from the mean of the 2 diameters.

$$S = \pi 4 \times \text{mean}(D1;D2)2$$

The final surface area after migration of the deposit S24 h is calculated from the mean of the 2 diameters.

The migration index is the ratio

S24 h+S0

The higher the diffusion index, the greater the migration of the formula.

Protocol for Evaluating the Tack

The tack is evaluated by a panel of sensory experts made up of 10 individuals. Each composition is applied to the forearm at a dose of 2 mg/cm$^2$. The product is spread by circular movements until it had penetrated (approximately 30 seconds). The tack is evaluated after 2 minutes of drying, by applying the back of the hand to the treated area, according to a scale ranging from 1 to 15 wherein 1 constitutes a very tacky reference and 15 constitutes a non-tacky reference.

Protocol for Evaluating the Greasy Appearance

The greasy appearance is evaluated by a panel of sensory experts made up of 10 individuals. Each composition is applied to the forearm at a dose of 2 mg/cm$^2$. The product is spread by circular movements until it had penetrated (approximately 30 seconds). The greasy appearance is evaluated with a finger after 2 minutes of drying according to a scale ranging from 1 to 15, where 1 represents a very greasy reference and 15 constitutes a sparingly greasy reference.

Protocol for Evaluating the Sprayability of the Compositions

The spray quality or sprayability is evaluated by the uniformity and evenness of the trace obtained by spraying each composition at a distance of 15 cm from a black paper support (1 press on the pushbutton).

The pump used is a PZ2 DLE PSK pump (Aptar) with a DU3527 nozzle.

The uniformity and evenness of the impact of the product sprayed on the surface are evaluated on a scale of 1 to 5 (where 1 represents a non-uniform and uneven impact and 5 represents a uniform even impact.

Results

TABLE I

| | A | B | C | D | E |
|---|---|---|---|---|---|
| VISCOSITY (in cP) | 120 | 95 | 130 | 86 | 90 |
| Vitro SPF | 72.5 ± 5.4 | 71.0 ± 4.4 | 69.7 ± 7.7 | 71.9 ± 4.2 | 75.1 ± 6.3 |
| MIGRATION INDEX | 119 | 22 | 89 | 84 | 67 |
| Spray impact quality score | 2 | 1 | 3 | 5 | 5 |
| Non-tacky finish (Score by sensory expert panel, out of 15; 1 = Very tacky; 15 = Non-tacky) | 5.6 ± 0.6 | 10.3 ± 1.9 | 11.5 ± 0.5 | 11.4 ± 1.2 | 10.7 ± 1.2 |
| Non-greasy finish (Score by sensory expert panel, out of 15; 1 = Greasy finish; 15 = Non-greasy finish) | 6.3 ± 1.2 | 8.6 ± 0.3 | 10.1 ± 1.9 | 10.4 ± 0.6 | 10.0 ± 0.9 |
| STABILITY 2 months 45° C. | Compliant | Compliant | Creaming | Compliant | Compliant |

The plates are deposited on a hot plate at 32° C., which is skin temperature.

The diameters of the deposit are taken at T24 h using a graduated ruler on the 2 diagonals.

These results show that the combination of a mixture of particular diesters and of a dialkyl ether, and of at least one UV-screening agent in an aqueous composition makes it possible to obtain a stable photoprotective composition which has a good SPF, good cosmetic properties, limited migration and also excellent sprayability. The compositions according to the invention are non-greasy and non-tacky.

EXAMPLES F TO J

Vaporizable fluid antisun formulations according to the invention containing the following ingredients were prepared.

| INCI name | Phase | F | G | H | I | J |
|---|---|---|---|---|---|---|
| AQUA | A1 | QS 100 | QS 100 | QS 100 | QS 100 | QS 100 |
| PROPANEDIOL | A1 | 2.5 | 2.5 | 2.5 | 2.5 | 2.5 |
| GLYCEROL | A1 | 6.0 | 6.0 | 6.0 | 6.0 | 6.0 |
| TRISODIUM ETHYLEDIAMINE DISUCCINATE | A1 | 0.3 | 0.3 | 0.3 | 0.3 | 0.3 |
| ACRYLATES COPOLYMER (AQUA SF1) | A1 | 2.0 | 2.0 | 2.0 | 2.0 | 2.0 |
| TRIETHANOLAMINE | A1 | 0.1 | 0.1 | 0.4 | 0.1 | 0.1 |
| BUTYLMETHOXYDIBENZOYL METHANE | B | 5 | 5 | 5 | 5 | 5 |
| ETHYLHEXYL SALICYLATE | B | 5 | 5 | 5 | 5 | 5 |
| ETHYLHEXYL TRIAZONE | B | 2 | 2 | 2 | 2 | 2 |
| OCTOCRYLENE | B | 7 | 7 | 7 | 7 | 7 |
| HOMOSALATE | B | 10 | 10 | 10 | 10 | 10 |
| C12-22 ALKYL ACRYLATE/ HYDROXYETHYLACRYLATE COPOLYMER | B | 2 | 2 | | | |
| STEARIC ACID | B | | | 1.5 | | |
| GLYCERYL STEARATE (and) PEG-100 STEARATE | B | | | 2 | | |
| POLYESTER-5 | | | | | 2 | |
| BEHENYL ALCOHOL (and) GLYCERYL STEARATE (and) DISODIUM ETHYLENE DICOCAMIDE PEG-15 DISULFATE (and) GLYCERYL STEARATE CITRATE | | | | | | 2 |
| DIISOPROPYL ADIPATE | B | 5 | 3 | 4 | 4 | 2 |
| DICAPRYLYL ETHER | B | 5 | 3 | 4 | 3 | 2 |
| DIISOPROPYL SEBACATE | B | 2 | 3 | 4 | 3 | 6 |
| PHENOXYETHANOL | B | 0.5 | 0.5 | 0.5 | 0.5 | 0.5 |
| CAPRYLYL GLYCOL | B | 0.3 | 0.3 | 0.3 | 0.3 | 0.3 |
| CITRIC ACID | C | 0.07 | 0.07 | 0.07 | 0.07 | 0.07 |
| DENATURED ALCOHOL (absolute ethanol) | D | 3 | 3 | 3 | 3 | 3 |

Compositions F to J are stable with a good SPF, good cosmetic properties, limited migration and also excellent sprayability.

Furthermore, the compositions according to the invention are non-greasy and non-tacky.

The invention claimed is:

1. A fluid aqueous composition intended for the protection of keratin materials against ultraviolet radiation, which comprises at least:
    (a) a photoprotective system capable of screening out UV radiation in an amount ranging from 0.1% to 40% by weight relative to the total weight of the composition,
    (b) at least one diester of a $C_2$-$C_8$ carboxylic acid and of a $C_1$-$C_4$ alcohol in an amount ranging from 0.1% to 10% by weight relative to the total weight of the composition,
    (c) at least one diester of a $C_9$-$C_{14}$ carboxylic acid and of a $C_1$-$C_4$ alcohol in an amount ranging from 0.1% to 10% by weight relative to the total weight of the composition, and
    (d) at least one $C_4$-$C_{26}$ dialkyl ether in an amount ranging from 0.1% to 10% by weight relative to the total weight of the composition.

2. The composition as claimed in claim 1, wherein the diester(s) of a $C_2$-$C_8$ carboxylic acid and of a $C_1$-$C_4$ alcohol b) are chosen from the compounds of formula (I):

$$R1-O-CO-X-CO-O-R2 \quad (I)$$

wherein:
    R1 and R2, which may be identical or different, are chosen from $C_1$-$C_4$ linear alkyls, $C_3$-$C_4$ branched alkyls and mixtures thereof,
    X is a $C_2$-$C_6$, linear or branched, hydrocarbon-based divalent radical.

3. The composition as claimed in claim 1, wherein the diester of a $C_2$-$C_8$ carboxylic acid and of a $C_1$-$C_4$ alcohol b) is diisopropyl adipate.

4. The composition as claimed in claim 1, wherein the diester b) is present in the composition in amounts ranging from 0.5% to 8% by weight relative to the total weight of the composition.

5. The composition as claimed in claim 1, wherein the diester(s) of a $C_9$-$C_{14}$ carboxylic acid and of a $C_1$-$C_4$ alcohol c) are chosen from the compounds of formula (II):

$$R1-O-CO-X-CO-O-R2 \quad (II)$$

wherein
    R1 and R2, which may be identical or different, are chosen from $C_1$-$C_4$ linear alkyls, $C_3$-$C_4$ branched alkyls and mixtures thereof
    X is a $C_7$-$C_{12}$ linear or branched hydrocarbon-based divalent radical.

6. The composition as claimed in claim 1, wherein the diester of a $C_9$-$C_{14}$ carboxylic acid and of a $C_1$-$C_4$ alcohol c) is diisopropyl sebacate.

7. The composition as claimed in claim 1, wherein the diester c) is present in the composition in amounts ranging from 0.5% to 8% by weight relative to the total weight of the composition.

8. The composition as claimed in claim 1, wherein the diether d) is of formula (III),

$$R5-O-R6 \qquad (III)$$

wherein R5 et R6, which may be identical or different, denote a $C_6$-$C_{25}$ linear or branched, alkyl or alkenyl radical.

9. The composition as claimed in claim 1, wherein the diether d) is present in the composition in amounts ranging from 0.5% to 8% by weight relative to the total weight of the composition.

10. The composition as claimed in claim 1, wherein the photoprotective system comprises one or more hydrophilic, lipophilic or insoluble organic screening agents and/or one or more mineral nanopigments.

11. The composition as claimed in claim 10, wherein the photoprotective system comprises at least one hydrophilic, lipophilic or insoluble organic screening agent.

12. The composition as claimed in claim 10, wherein the organic screening agents are chosen from; anthranilates; cinnamic derivatives; dibenzoylmethane derivatives; salicylic derivatives; camphor derivatives; triazine derivatives; benzophenone derivatives; β,β-diphenylacrylate derivatives; benzotriazole derivatives; benzalmalonate derivatives; benzimidazole derivatives; imidazolines; bis-benzazolyl derivatives; p-aminobenzoic acid (PABA) derivatives; methylenebis(hydroxyphenylbenzotriazole) derivatives; screening polymers and screening silicones; a-alkylstyrene-based dimers; 4,4-diarylbutadienes; and mixtures thereof.

13. The composition as claimed in claim 12, wherein the organic screening agents are chosen from
Ethylhexyl methoxycinnamate,
Ethylhexyl salicylate,
Homosalate,
Butyl methoxydibenzoylmethane,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyldibenzimidazoletetrasulfonate,
Methylenebis(benzotriazolyl)tetramethylbutylphenol,
Bis-ethylhexyloxyphenol methoxyphenyl triazine,
Ethylhexyl triazone,
Diethylhexyl butamidotriazone,
2,4,6-Tris(dineopentyl 4'-aminobenzalmalonate)-s-triazine,
2,4,6-Tris(diisobutyl 4'-aminobenzalmalonate)-s-triazine,
2,4-Bis(n-butyl 4'-aminobenzoate)-6-(aminopropyltrisiloxane)-s-triazine,
2,4-Bis(dineopentyl 4'-aminobenzalmalonate)-6-(n-butyl 4'-aminobenzoate)-s-triazine,
2,4-Bis(n-butyl 4'-aminobenzalmalonate)-6-[(3-{1,3,3,3-tetramethyl-1-[(trimethylsilyl)oxy]disiloxanyl}propyl)amino]-s-triazine,
2,4,6-Tris(diphenyl)triazine,
2,4,6-Tris(terphenyl)triazine,
Phenylene bis-diphenyltriazine
Drometrizole trisiloxane,
Polysilicone-15,
1,1-Dicarboxy(2,2'-dimethylpropyl)-4,4-diphenylbutadiene,
2,4-bis[5-(1-Dimethylpropyl)benzoxazol-2-yl-(4-phenyl)imino]-6-(2-ethylhexyl)imino-1,3,5-triazine,
and mixtures thereof.

14. The composition as claimed in claim 10, wherein the mineral UV-radiation-screening agents are chosen from coated or uncoated metal oxides.

15. The composition as claimed in claim 1, wherein the photoprotective system is present in a content ranging from 5% to 25% by weight relative to the total weight of the composition.

16. The composition as claimed in claim 1, wherein the viscosity is less than or equal to 0.5 Pa·s.

17. The composition as claimed in claim 1, wherein it the composition is an aqueous composition in a vaporizable form.

18. A pressurization device comprising at least (A) a reservoir containing at least one vaporizable fluid composition as claimed in claim 1 and (B) means for pressurizing said composition.

19. The device as claimed in claim 18, wherein the device is a non-aerosol pump.

20. The device as claimed in claim 18, wherein the device is an aerosol container or an aerosol pump.

21. The device as claimed in claim 17, wherein the device is a two-compartment aerosol container or aerosol pump.

22. A method of reducing or eliminating the effect of migration of a composition in a physiologically acceptable aqueous support, and comprising at least one photoprotective system capable of screening out UV radiation out of the application area on keratin materials by including in the composition at least one mixture of (b) at least one diester of a $C_2$-$C_8$ carboxylic acid and of a $C_1$-$C_4$ alcohol, (c) at least one diester of a $C_9$-$C_{14}$ carboxylic acid and of a $C_1$-$C_4$ alcohol, and (d) at least one $C_4$-$C_{26}$ dialkyl ether.

23. A method of improving the cosmetic pleasantness and the comfort of use of a cosmetic composition in the form of an oil-in-water emulsion or water-in-oil-in-water multiple emulsion comprising, in a physiologically acceptable medium, and comprising at least one UV-radiation-absorbing agent by including in the composition at least one mixture of (b) at least one diester of a $C_2$-$C_8$ carboxylic acid and of a $C_1$-$C_4$ alcohol, (c) at least one diester of a $C_9$-$C_{14}$ carboxylic acid and of a $C_1$-$C_4$ alcohol, and (d) at least one $C_4$-$C_{26}$ dialkyl.

24. The composition as claimed in claim 1, wherein the diester b) is present in the composition in an amount ranging from 0.5% to 8% by weight relative to the total weight of the composition; the diester c) is present in the composition in an amount ranging from 0.5% to 8% by weight relative to the total weight of the composition; the diether d) is present in the composition in an amount ranging from 0.5% to 8% by weight relative to the total weight of the composition; and the photoprotective system is present in an amount ranging from 5% to 25% by weight relative to the total weight of the composition.

25. The composition as claimed in claim 1, wherein the diester b) is present in the composition in an amount ranging from 1% to 5% by weight relative to the total weight of the composition; the diester c) is present in the composition in an amount ranging from 1% to 5% by weight relative to the total weight of the composition; the diether d) is present in the composition in an amount ranging from 1% to 5% by weight relative to the total weight of the composition; and the photoprotective system is present in an amount ranging from 5% to 25% by weight relative to the total weight of the composition.

* * * * *